United States Patent [19]

Diepenhorst et al.

[11] Patent Number: 5,849,664
[45] Date of Patent: Dec. 15, 1998

[54] COMPOSITION SUITABLE FOR INHIBITING POTATO SPROUTING AND/OR FUNGOID GROWTH

[75] Inventors: Pieter Diepenhorst, Heesch; Klaasje Jannie Hartmans, Bennekom; Franciscus Johannes van Kleef, Holthees, all of Netherlands

[73] Assignee: B.V. Chemische Pharmaceutische Industrie "Luxan", PA Elst, Netherlands

[21] Appl. No.: 624,410

[22] PCT Filed: Oct. 3, 1994

[86] PCT No.: PCT/NL94/00240

§ 371 Date: Sep. 20, 1996

§ 102(e) Date: Sep. 20, 1996

[87] PCT Pub. No.: WO95/09536

PCT Pub. Date: Apr. 13, 1995

[30] Foreign Application Priority Data

Oct. 4, 1993 [NL] Netherlands ............................ 9301703

[51] Int. Cl.⁶ ............................ A01N 31/00; A01N 35/00
[52] U.S. Cl. ........................ 504/418; 504/348; 504/353; 514/690; 514/729
[58] Field of Search ................................... 504/118, 353, 504/348; 514/729, 690

[56] References Cited

U.S. PATENT DOCUMENTS 5,139,562   8/1992   Vaughn et al. ............................... 71/88

FOREIGN PATENT DOCUMENTS 675573   12/1963   Canada .
2142709   5/1990   Japan .
5139924   8/1993   Japan .
9210934   7/1992   WIPO .

OTHER PUBLICATIONS

Meigh, J. Sci. Fd. Agric., 1969, vol. 20, Mar. pp. 159–164.

*Primary Examiner*—Allen J. Robinson
*Attorney, Agent, or Firm*—Evenson, McKeown, Edwards & Lenahan, P.L.L.C.

[57] ABSTRACT

A composition suitable for inhibiting potato sprouting and inhibiting the growth of fungi and decay bacteria, including a mixture of carvone and menthol, a method for inhibiting potato sprouting by using such composition and the use thereof, and a composition in the form of an emulsion or granulate which includes carvone and menthol or carvone alone, giving rise to a delayed release of the active compound and an extension of the length of sprout inhibition.

10 Claims, 2 Drawing Sheets

COMPOSITION SUITABLE FOR INHIBITING POTATO SPROUTING AND/OR FUNGOID GROWTH

This application is a 371 of PCT/NL94/00240, filed Oct. 3, 1994.

FIELD OF THE INVENTION

This invention relates to a composition which is suitable for inhibiting potato sprouting and/or fungoid growth, and to the use of that composition in controlling patato sprouting and/or fungoid growth in potatoes.

BACKGROUND OF THE INVENTION

Potato sprouting, also referred to as shooting, poses a problem in the storage of potatoes. In fact, sprouting leads to potato quality loss because it results in loss of weight, the turgor of the potatoes lessens (the potatoes become softer) and toxic products may be formed in the sprouts.

Sprouting can be inhibited by storing the potatoes at a temperature of 2° C., but at such a low temperature reducing sugars are formed which give a brown color to the potatoes when (deep)fried and cause them to taste sweet. For this reason the potatoes are typically stored at a temperature between 5° and 8° C. At such a temperature the problem of the formation of reducing sugars is absent or considerably smaller, but sprouting upon prolonged storage is not entirely avoided.

Therefore, sprouting inhibitors are necessary to maintain potato quality during storage, both in potatoes intended for direct consumption and in potatoes to be processed into potato products. Such sprouting inhibitors are used to inhibit sprouting over prolonged storage periods at lower temperatures, i.e. below 10° C.

Chemical sprouting inhibitors have been utilized with success for over two decades to prevent sprouting or shooting during the storage of potatoes. Propham (IPC) and chlorpropham (CIPC), which were originally developed as herbicides, are utilized as sprout inhibitors on a large scale in Europe, while in America maleic acid anhydride is used as well. In England, tecnazene is still being used as a sprout inhibitor.

These last two inhibitors are probably going to be forbidden in the near future. Nor is the future of IPC and CIPC certain, since there is a tendency to lower the maximum residue level (MRL) of such compounds on potatoes. Also, the market for untreated potatoes (i.e. potatoes not treated with chemicals) is rapidly expanding.

Accordingly, there is a need for alternatives to these sprout inhibitors.

Replacement sprout inibitors must satisfy the following requirements:

they must preferably be effective at a low dose and easy to use;

they must preferably be of vegetable origin, non-toxic, colorless, tasteless and odorless;

they must not affect the properties of the potatoes or their processability; and they must be acceptable in connection with the regulations applicable to such products.

Products which satisfy these requirements have been known to date. A number of monoterpenes from plants show interesting possibilities as alternative sprout inhibitors. One of these compounds is carvone, which compound is present in the essential oil of the seeds of the caraway plant (*Carum carvi*). This compound is also of interest because it is registered as a food additive and has the so-called "GRAS" status (Generally Recognized As Safe). Moreover, it is possible to grow caraway on a commercial scale. This is already happening on a large scale in various countries both inside and outside Europe.

Caraway seed contains approximately 3 to 5% essential oil. Approximately one-half thereof consists of D-carvone, the other half is D-limonene, in addition to a few percent of other isoprenoids. D-limonene does not have sufficient influence on sprouting and can be removed through fractionated distillation, so that a D-carvone enriched (90–95%) caraway oil is obtained.

D-carvone further occurs in the essential oil of dill seed. L-carvone, which is also active, occurs in the essential oil of citrus and some varieties of mint.

The sprouting inhibitory activity of carvone has long been known. J.Sci.Fd Agric., vol. 20, March 1969 already describes the sprouting inhibiting activity of carvone in potatoes.

Beveridge et al., Potato Res. 24 (1981), pp. 61–76, compared the sprout inhibitory effect of carvone with other compounds and concluded that carvone was not considered suitable for commercial purposes because of its too low activity as a sprouting inhibitor.

In Potato World, vol. 2, no. 4 (1985), pp. 36–38 Duncan and Boyd demonstrated the effectiveness of carvone as a sprouting inhibitor, but they also mentioned that the volatility of this agent is so high that it was not eligible for commercial use.

Other sprout inhibitors are known which satisfy the above-mentioned requirements. European patent application 0 287 946 describes the sprout inhibitory effect of mint oil. This oil can be used to inhibit sprouting or to stop or interrupt any sprouting which has already developed. The advantage of the use of mint oil is that after the treatment the potatoes are directly suitable for sale without requiring that a waiting period be observed between treatment and sale or processing.

However, it is impossible to preclude the possibility that mint oil, which has a strong taste and odor, adversely affects the sensory properties of the potato.

U.S. Pat. No. 5,739,562 discloses the sprouting inhibitory activity of monoterpenes, coming inter alia from peppermint oil and spearmint oil. These oils comprise inter alia menthol as active sprout inhibitory compound.

SUMMARY OF THE INVENTION

Surprisingly, it has now been found that the combination of carvone and menthol as sprouting inhibitor has a synergistic effect, as a result of which sprouting in potatoes is inhibited longer than in the case where carvone or menthol is used separately.

This sprouting agent based on a combination of menthol and carvone can be used with different crops, including grains and tubers.

The sprouting agent according to the invention also has an inhibitory effect on the development of fungi and decay bacteria.

Accordingly, the invention is characterized in that the composition to be used as sprouting inhibitor or inhibitor on the development of fungi and decay bacteria comprises a mixture of carvone and menthol.

The composition according to the invention is particularly suitable for use with ware potatoes and industrial potatoes.

The composition according to the invention can also be used to temporarily inhibit the sprouting of seed-potatoes.

Preferably, carvone and menthol are present in the composition in a mixture having a weight ratio in the range of 99:1 to 1:99, more preferably in the range of 90:10 to 10:90, even more preferably in the range of 20:1 to 1:1, and most preferably in the range of 8:1 to 2:1.

It is preferred to use an excess of carvone in connection with the sensory aspects (in particular the strong odor and taste) of menthol.

The carvone used can be D-carvone as well as L-carvone or a mixture of D- and L-carvones, and may be of vegetable origin or semivegetable through preparation by chemical conversion from, for instance, citrus waste.

D-carvone and L-carvone exhibit an equally high activity and both may therefore be effectively used, separately as well as in a mixture.

The menthol used can be DL menthol, which is commercially available as a product with a purity of, for instance, minimally 99%. Other isomers of menthol can be used as well.

The composition can be used dry as a powder or granulate which is imparted to the potatoes as the storage space is being filled with them (this is the so-called basic treatment).

Instead of being used in the form of a powder or granulate, the composition can also be misted over the potatoes while they are being stored in the barn, as a liquid or an emulsion, either pure or mixed with a small amount of water.

Furthermore, composition can also be contacted with the potatoes at a later stage during the storage period by misting the composition in the storage space with the support of fans in that space.

In that case, depending on the desired form of application, the composition can also comprise a suitable carrier, suitable solvents, fillers or other substances conventionally present.

Suitable powdery or granular carriers and fillers are starch and starch derivatives, clay, talcum and other silicas, sand, diatomaceous earth, calcium carbonate and calcium sulfate (gypsum) and the various (co)polymers which can be used as carriers.

For making a granulate, an inert carrier can be mixed with menthol and then be impregnated with carvone in the desired ratio.

Granules can also be sprayed with a mixture of menthol and carvone.

Suitable for the application of the composition in a liquid form are the solvents of mineral origin, including aliphatic or aromatic solvents or mixtures thereof, which may or may not be chlorinated. Examples of these solvents are xylene, dichloromethane, ketones, aldehydes, alcohols such as glycerols (for instance polyethylene glycol), or derivatives or mixtures thereof. It is also possible to use solvents of animal or vegetable origin, such as linseed oil, soy bean oil or derivatives thereof. It is also possible to use mixtures of such solvents of animal, vegetable and mineral origin.

A paste can be formed by adding thickeners, such as, for instance, synthetic or natural polymeric thickeners, to solutions and emulsions of the composition in the above-mentioned solvents.

Suitable emulsifying agents for preparing an emulsion are cationic, anionic and non-ionic surface-active substances of animal, vegetable and mineral origin. Examples are Ca-dodecyl benzene sulfonates, nonyl phenol polyglycol ethers, ethoxylated fatty acid alcohols or amines or derivatives or combinations thereof.

For preparing an emulsion, carvone and menthol can be mixed in the desired ratio, whereafter an emulsifier is added and optionally water or another solvent.

The emulsifier or the mixture of emulsifiers is preferably present in a ratio of about 4:1 in relation to the active compound. The eventual emulsion preferably contains between 20 and 50 wt. % of active compound.

In connection with the present invention it is noted that the suitability of the various components of the formulation is partly determined by the requirements imposed on substances which come into contact with human or animal foods in general and in particular by the requirements regarding their safety for humans, animals and the environment.

The extension of the active period that can be achieved through the use of the composition according to the present invention as sprout inhibitor may run up to one-quarter of the normal active period, so that a total active period of up to 1.25 times the normal active period is obtained.

It is also possible, of course, to exploit the increased activity of the composition according to the present invention to reduce the amount active compound to be used. This does not so much effect a prolonged sprouting inhibition or inhibition of the growth of fungi and decay bacteria as a reduction of the amount of agent to be used, which can lead to a considerable saving of costs.

A further aspect of the invention relates to the formulation of the sprouting inhibitor.

Surprisingly, if the mixture is an emulsion in water or in an aqueous solution, a delayed release of the active compounds has been found to arise, so that the active agent remains present in the space longer, the active life of the agent thereby being extended even further.

It has moreover been found, surprisingly, that an extension of the effective life of the composition in this manner can also be realized if carvone alone is present as active agent.

Accordingly, the invention also relates to a composition in the form of an emulsion in water or in an aqueous solution, with carvone or a mixture of carvone and menthol being present as active agent.

The use of the composition according to the invention will be elucidated hereinafter.

First, however, the conventional storage methods for potatoes will be described.

It is conventional to store the potatoes in bulk or in large boxes in the storage space, which is mostly insulated. By means of fans, cooler outside air can be passed through the potatoes. Optionally, the (outside) air can additionally be cooled further by means of cooling systems before being passed through the potato mass.

Storage in an outside pit or in a clamp silo is used for industrial potatoes nowadays, but a variant of this can also be used to store ware potatoes. This last, however, is less conventional.

Also, for the storage of potatoes, use can be made of cells or boxes with contents corresponding with the capacity of ventilation, heating and delivery of the product.

The bulk potatoes are first dried, stored for a few days at about 15° C. and then cooled in about two weeks to the desired storage temperature to ensure a good injury healing of damaged potatoes. This period of injury healing is necessary to limit microbial attack and weight losses during storage. The injury healing period of the lot takes about 14 days. After the injury healing period, the potatoes are stored at the desired storage temperature, the temperature being controlled through fresh air cooling or mechanical cooling. The desired storage temperature is 2°–4° C. for seed-potatoes, 4°–6° C. for ware potatoes, 5°–8° C. for French fries and dry industry, and 7°–10° C. for chips.

After a sprouting dormancy of a few months after harvest, the potato begins to exhibit an inclination to sprout (depending on variety, history and storage method). In the course of time, this inclination to sprout grows increasingly stronger.

If cooling takes place in mechanical manner (so that the desired storage temperature can be reached rapidly), the chances of early sprouting are limited already. To inhibit sprouting in optimum manner, subsequently the composition according to the present invention is used.

The use of the composition according to the invention as sprout inhibitor and as inhibitor of the development of fungi and decay bacteria is now further elucidated.

The so-called basic treatment consists of imparting the composition (in the form of, for instance, powder or granules), for instance on a conveyor which conveys the potatoes to the storage space It is also possible to spray or atomize the composition over the potatoes (above the conveyor).

It is also possible to pass the composition to the storage space via the ventilation system. For this manner of application, the agent can for instance be atomized or sprayed in the air. For this purpose it is possible to combine a mixture of carvone and menthol with a gaseous carrier so as to facilitate their introduction into the air stream.

The two treatments can also be combined or be performed one after the other.

In all cases, the composition will evaporate to a greater or lesser extent and accordingly all potatoes to be treated will come into contact with the active agent.

The application of the composition preferably takes place in a manner such that the concentration of carvone and menthol together in the air of the storage space is between about 2 and 20 $\mu$g/l air and more particularly between about 5 and 10 $\mu$g/l air. In this way the inhibitory effect on the growth of fungi and bacteria is guaranteed. At values lower than about 5 $\mu$g/l air, the sprouting inhibition will not be guaranteed to a sufficient extent. Higher values than about 20 $\mu$g/l air do not lead to a longer sprout inhibition and therefore lead only to an unduly large use of sprout inhibiting agent.

DETAILED DESCRIPTION OF THE PREFERRED EMBODIMENTS

Figure 1:
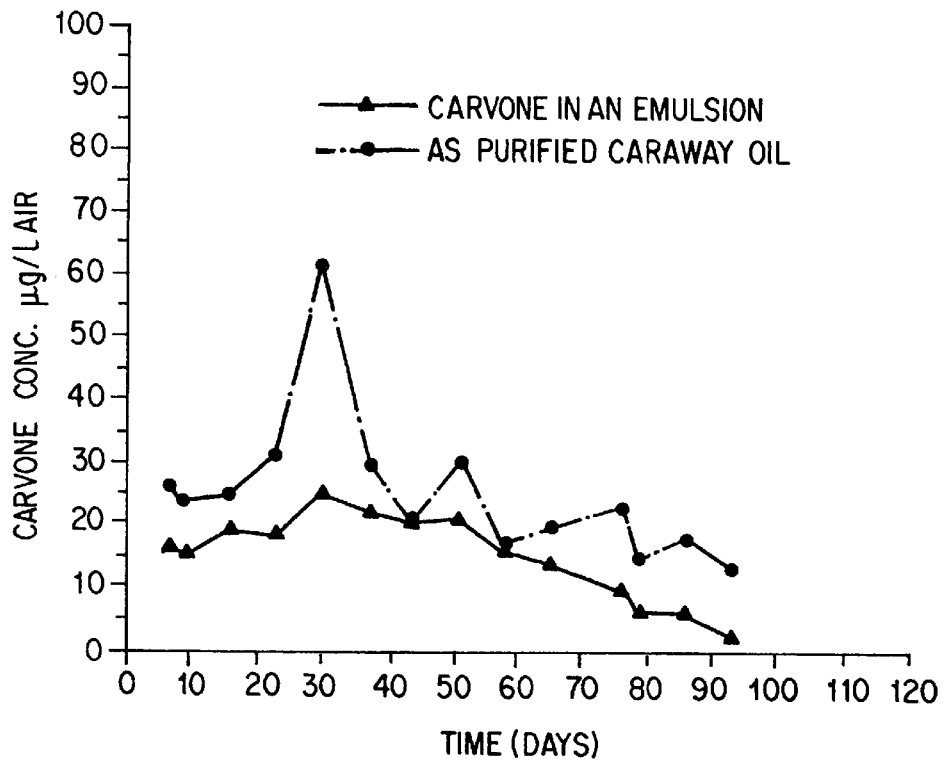
FIG. 1 is a graphical representation of the concentration of carvone in the air, with respect to time when using carvone in an emulsion and as purified caraway oil.

The invention will now be further explained in and by the following Examples.

Example I

Sprout inhibiting activity

Ware potatoes of the variety 'Bintje' went through an injury healing period after harvest at a temperature of 15° C. and were then stored at 6° C. For the experiment, in each case a number of 30 potatoes (size 45–55) were treated with a sprout inhibitor having one of the compositions according to the Table below.

The sprout inhibitor was prepared by directly mixing carvone and menthol in the amounts according to the Table.

The treatment of the potatoes was effected by providing the sprout inhibitor on the bottom of a glass vessel, whereafter a rack was arranged above the vessel, the potatoes were arranged on the rack and the vessel was closed with a lid.

The potatoes were then kept at a temperature of 6° C. Twice a week the air in the vessel was refreshed by opening the lid of the storage space for one hour.

It was then observed after how many weeks of storage 80% of the tubers had sprouts longer than 1 cm.

The results are shown in Table 1 below.

'I' and 'II' in the Tables below indicate repeats of the same tests (duplicates).

TABLE 1

| Composition | | Effectiveness* | |
| --- | --- | --- | --- |
| carvone (mg) | menthol (mg) | I | II |
| 112.5 | 12.5 | 27 | 30 |
| 100 | 25 | 34 | 34 |
| 87.5 | 37.5 | 38 | >40 |
| 62.5 | 62.5 | >40 | >40 |

*Number of weeks until 80% of the tubers had sprouts longer than 1 cm.

Comparative Example 1

The method of Example I was repeated, with the understanding that either carvone alone or methol alone was used as sprout inhibitor. The results are shown in Table 2 below.

TABLE 2

| Composition | | Effectiveness* | |
| --- | --- | --- | --- |
| carvone (mg) | menthol (mg) | I | II |
| 62.5 | — | 17 | 15 |
| 87.5 | — | 18 | 20 |
| 100 | — | 20 | 21 |
| 112.5 | — | 21 | 24 |
| — | 12.5 | 15 | 14 |
| — | 25 | 26 | 30 |
| — | 37.5 | 30 | 30 |
| — | 62.5 | 34 | 34 |

*Number of weeks until 80% of the tubers had sprouts longer than 1 cm.

It is clear that the use of a mixture of carvone and menthol leads to an extended duration of effectiveness.

Example II

Delayed release

Ware potatoes of the variety 'Bintje' were given the same pretreatment as in Example I.

For this experiment, per formulation a number of 20 potatoes (size 45–55), with any sprouts removed, were used.

The potatoes were assembled in an exsiccator of a volume of 20 liters in the same manner as in experiment I with:

(1) 1297 mg of an emulsion containing 37 wt. % of carvone or (2) 505 µl purified caraway oil (contains 95 wt. % carvone).

The composition of the emulsion is as follows:

| carvone* | 37 wt. % |
|---|---|
| Toximul ™ 7356 B (Stepan, U.S.A.)** | 6 wt. % |
| Soprophor ™ BSU (Rhône-Poulenc)** | 2 wt. % |
| water | up to 100 wt. % |

*the amount of carvone is achieved by using 39 wt. % of purified caraway oil, which contains 95 wt. % carvone.
**emulsifier mixture, comprising anionic and non-ionic surface-active substances.

The amounts are such that about 480 mg carvone is present per exsiccator and hence per 20 potatoes.

The potatoes were then kept at a temperature of 6° C. Once a week an air sample was taken and twice a week the air in the space was refreshed by removing the lid from the exsiccator for a while.

The concentration of carvone in the air was measured.

The graph (FIG. 1) plots the concentration of carvone in the air when using carvone in an emulsion and as purified caraway oil (=comparative test) for the duration of the experiment.

It is known that if the concentration of carvone in the air of the storage space falls below 5 µg/l, sprouting of the potatoes will occur within a few weeks. It is therefore important that the concentration of carvone remain above this minimum value.

It follows from the graph that the concentration of carvone when using caraway oil decreases faster than in the case where carvone is used in an emulsion. When using the emulsion, the concentration of carvone falls below 5 µg/l after about 80 days. As a result, sprouting of the potatoes will follow within a few weeks.

When using carvone in the emulsion, the concentration of carvone is still higher than 10 µg/l after 90 days. Sprouting of the potatoes is thus inhibited longer.

Example III

Delayed release

Ware potatoes of the variety 'Bintje' were given the same pretreatment as in Examples I and II.

For this experiment, per formulation a number of 30 potatoes (size 45–55), with any sprouts removed, were used.

The following formulations were tested for their delayed release properties:

A: mist formulation containing:
71 wt. % d-carvone
24 wt. % dl-menthol.
B: emulsion containing:
24 wt. % d-carvone
6 wt. % dl-menthol
6 wt. % Tensiofix HVO
2 wt. % Soprophor
water to 100%.
C: granulate containing:
88 wt. % Tolsa sepiolite
9 wt. % d-carvone
3 wt. % dl-menthol.

The potatoes were assembled in an exsiccator of a volume of 2.7 liters in the same manner as in experiment I with:

(1) 107 µl of mist formulation A per container
(2) 333 µl of emulsion B per container
(3) 889 mg of a granulate C per container.

The potatoes were then kept at a temperature of 6° C. Once a week an air sample was taken and thrice a week the air in the space was refreshed by removing the lid from the exsiccator for a while.

The concentration of carvone and menthol in the air were measured.

Figure 2:
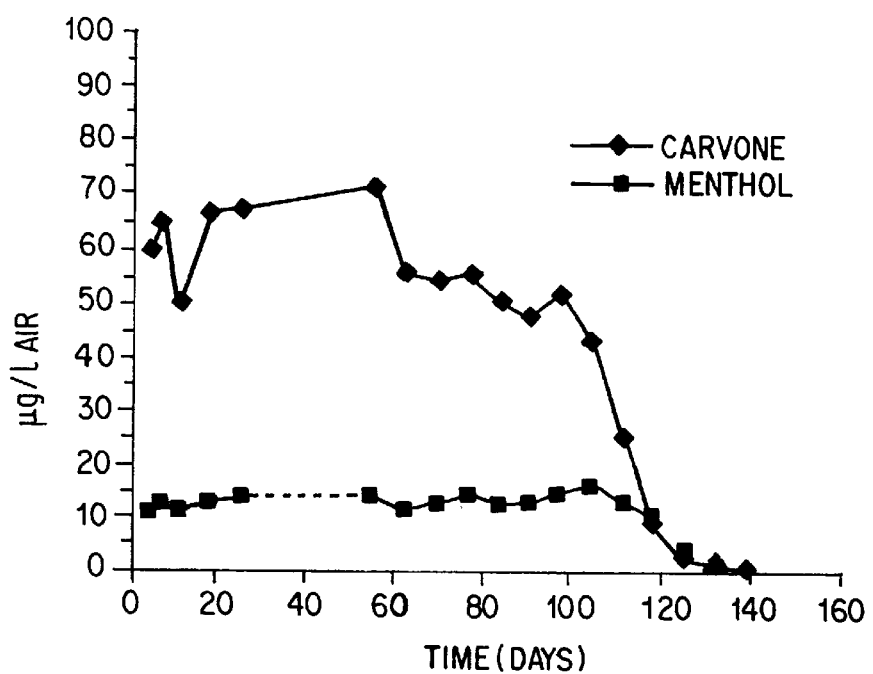
FIG. 2 is a graphical representation of the concentration of carvone and menthol in the air, with respect to time, when using a mist formulation.
Figure 3:
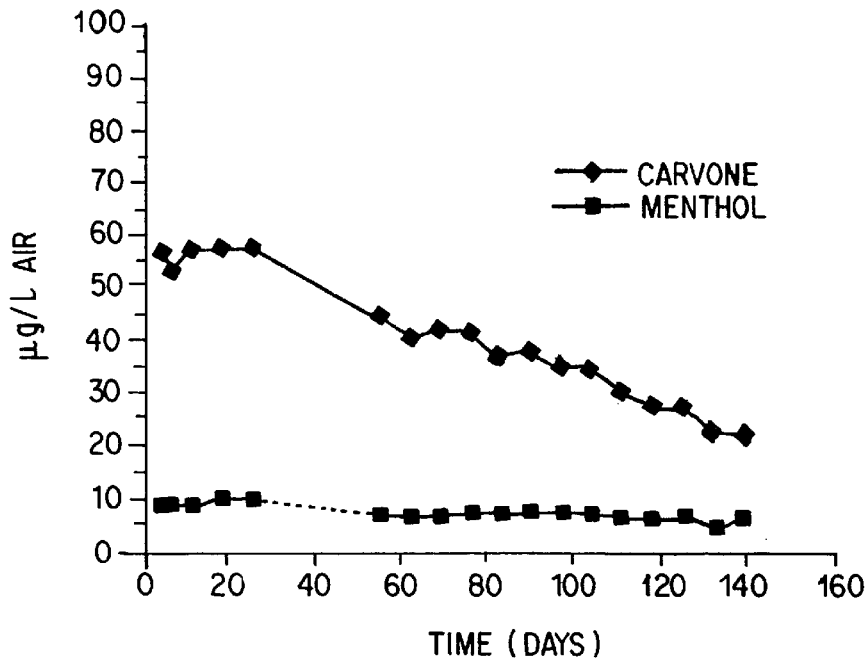
FIG. 3 is a graphical representation of the concentration of carvone and menthol in the air, with respect to time, when using an emulsion.
Figure 4:
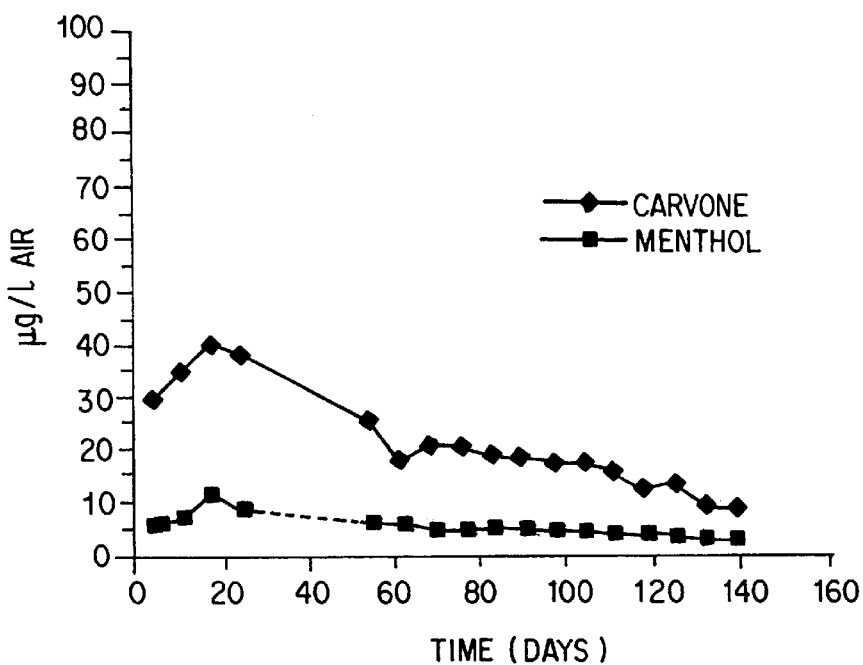
FIG. 4 is a graphical representation of the concentration of carvone and menthol in the air, with respect to time, when using a granulate.

The graphs (FIGS. 2–4) plot the concentration of carvone and menthol in the air when using a mixture of carvone and menthol in a mist formulation, in an emulsion and in a granulate for the duration of the experiment.

It follows from the graphs that the concentration of carvone and menthol decreases slower when these formulations are used than in the case where carvone is used as caraway oil (Experiment II).

Example IV

In this example, the synergistic activity of carvone and menthol in suppressing fungoid growth on potato tubers is demonstrated.

Potato tubers (Bintje, 45/50 mm, harvest 1993) were injured in a sterile manner. To each injury, 160 spores of the fungus *Fusarium sulphureum* (causing dry rot) were added. The tubers (30 pieces/container) were stored for 6 weeks at 10° C. in hermetically closed plastic containers in the presence of carvone, menthol or a carvone/menthol mixture. The examination of the attack was qualitative, on the basis of the percentage of injuries exhibiting dry rot. A comparison was made with tubers that had been stored in the absence of any compound. The rot development of these last tubers was assumed to be 100%. The results are shown in Table 3 below.

TABLE 3

| Compound applied/ rot dev. (%) | Carvone (µl) | Rot dev. (%) | Menthol (µl) | Rot dev. (%) | Carvone/ menthol (µl) | Rot dev. (%) |
|---|---|---|---|---|---|---|
| | 50 | 83 | 50 | 100 | 50/200 | 60 |
| | 125 | 73 | 125 | 100 | 125/125 | 40 |
| | 200 | 43 | 200 | 100 | 200/50 | 0 |
| | 250 | 0 | 250 | 80 | check | 100 |

This Table shows that in the presence of 200 µl carvone, still 43% of the rot development takes place, but in the presence of 250 µl carvone, this has been reduced to 0%.

50 µl menthol does not inhibit the rot development at all.

However, the combination of 200 µl carvone and 50 µl menthol suppresses fungoid growth completely.

This test shows that menthol enhances the activity of carvone synergistically.

We claim:

1. A composition for inhibiting potato sprouting or fungoid growth comprising synergistic effective amounts of carvone and menthol as a potato sprout inhibitor or a fungoid growth inhibitor.

2. A composition according to claim 1, wherein said composition comprises a mixture of carvone and menthol in a weight ratio of 90:10 to 10:90.

3. A composition according to claim 1, wherein said composition comprises a mixture of carvone and menthol in a weight ratio of 8:1 to 2:1.

4. A composition according to claim 1, wherein said composition further comprises a carrier.

5. A composition according to claim 1, wherein said composition is in a form selected from the group consisting of a solution, granules, a paste, an emulsion and a powder.

6. A composition according to claim 1, wherein said composition further comprises at least one member selected from the group consisting of solvents and fillers.

7. A composition to claim 1, wherein the composition is in a form selected from the group consisting of an emulsion in water and an emulsion in an aqueous solution.

8. A composition according to claim 1, wherein potatoes are contacted with the composition by misting, spraying, atomizing, scattering or evaporating said composition.

9. A method for inhibiting potato sprouting, comprising applying "to potatoes a synergistic effective potato sprouting inhibiting amount" of a composition according to claim 1.

10. A method according to claim 9, comprising contacting potatoes with the composition by a method selected from the group consisting of spraying, atomizing, scattering and evaporating said composition.

* * * * *